United States Patent

Kaufmann et al.

[11] Patent Number: 5,334,750
[45] Date of Patent: Aug. 2, 1994

[54] PROCESS FOR THE PREPARATION OF CINNAMIC ACID DERIVATIVES

[75] Inventors: Dieter Kaufmann, Bergisch Gladbach; Carsten Hesse, Leverkusen; Thomas Himmler, Odenthal, all of Fed. Rep. of Germany

[73] Assignee: Bayer Aktiengesellschaft, Leverkusen, Fed. Rep. of Germany

[21] Appl. No.: 40,726

[22] Filed: Mar. 31, 1993

[30] Foreign Application Priority Data

Apr. 7, 1992 [DE] Fed. Rep. of Germany ........ 4211608

[51] Int. Cl.⁵ .............................................. C07C 69/76
[52] U.S. Cl. ...................................... 560/104; 558/401; 562/495; 564/182
[58] Field of Search ........................ 560/104; 558/401; 564/182; 562/495

[56] References Cited

U.S. PATENT DOCUMENTS

| | | | |
|---|---|---|---|
| 4,156,785 | 5/1979 | Prange et al. | 560/206 |
| 4,564,479 | 1/1986 | Spencer | 549/370 |
| 4,713,473 | 12/1987 | Schudel et al. | 520/53 |
| 4,970,332 | 11/1990 | Casvcey | 560/104 |
| 5,187,303 | 2/1993 | Eisenstadt et al. | 560/55 |

FOREIGN PATENT DOCUMENTS

| | | |
|---|---|---|
| 186349 | 7/1986 | European Pat. Off. |
| 7021342 | 2/1982 | Japan |
| 2126152 | 6/1987 | Japan |

*Primary Examiner*—Paul J. Killos
*Attorney, Agent, or Firm*—Sprung Horn Kramer & Woods

[57] ABSTRACT

Cinnamic acid derivatives, in particular 2-ethylhexyl p-methoxycinnamate and 2-isoamyl p-methoxycinnamate, are prepared avoiding particular effort for workplace hygiene and ecology by using bromoaromatic and acrylic acid derivatives in the presence of palladium catalysts and a large excess of phosphane (based on the palladium), in the presence of an inorganic base and in the presence of alcohols and/or a phase transfer catalyst.

10 Claims, No Drawings

PROCESS FOR THE PREPARATION OF CINNAMIC ACID DERIVATIVES

The present invention relates to a process for the preparation of cinnamic acid derivatives, in which no particular effort in respect of solvents and bases is required.

It is already known that olefins can be arylated by halogenoaromatics in the presence of palladium catalysts, phosphane ligands and a base (see R. F. Beck, Org. React. 27, 345-391 (1982)).

The reaction is often carried out with various amines (for example triethylamine, tributylamine or tetramethylethylenediamine), which can simultaneously serve as solvents. Alkali metal carboxylates in dimethylformamide (see European Published Specification 78,768) or alkali metal carbonates or bicarbonates can also be employed as bases if a polar aprotic solvent (for example dimethylformamide, hexamethylphosphoric acid triamide or acetonitrile) and a phase transfer catalyst are also present (see Tetrahedron Lett. 26, 2667-2670 (1985) and J. Org. Chem. 56, 1289-1293 (1991)).

All of these base/solvent systems are aggressive media and require particular effort for their handling from toxicological and ecological aspects.

It is furthermore known from the Patent Application WO 90/10617 that p-methoxyaniline (=p-anisidine) can first be diazotised and then converted into 4-iodoanisole with potassium iodide in a two-stage process. This product can then be reacted with 2-ethylhexyl acrylate in the presence of triethylamine and a palladium catalyst to give 2-ethylhexyl 4-methoxycinnamate. Here also, triethylamine, which is in principle undesirable, is required, and the triethylammonium iodide which forms must be split back into triethylamine and alkali metal iodide with an alkali metal hydroxide solution. This process has a very large number of stages and requires the recovery of alkali metal iodide.

The reaction of 4-iodoanisole with methyl acrylate and a stoichiometric amount of tributylamine in the presence of 1 mol % of palladium(II) acetate gives, after 5 hours at 100° C., a yield of only 68% of methyl 4-methoxycinnamate (J. Org. Chem. 37, 2320-2322 (1972)).

The reaction of 4-bromoanisole with methyl acrylate and a stoichiometric amount of tetramethylethylenediamine in the presence of 1 to 2 mol % of palladium(II) acetate and 2 to 4 mol % of triphenylphosphane leads, after 36 hours at 135° C., to a yield of methyl 4-methoxycinnamate of 54% (J. Am. Chem. Soc. 96, 1133-1136 (1974)).

There is therefore the need for a process with which the bromoaromatics, which are less reactive but easier to prepare, can be reacted with acrylic acid derivatives in the presence of palladium catalysts in high space/time yields and using auxiliaries which require no particular effort.

A process has now been found for the preparation of cinnamic acid derivatives from bromoaromatics and acrylic acid derivatives in the presence of palladium catalysts and a phosphane, which is characterised in that it is carried out in the presence of an inorganic base, a large excess (based on the palladium) of phosphane, and alcohol and/or a phase transfer catalyst.

No amine nor solvent which requires particular effort to handle is required in this process.

The palladium can be added in any desired form in the process according to the invention. Palladium compounds of oxidation levels 0 and +2, for example palladium(II) halides and palladium(II) carboxylates, and complex palladium compounds, for example complex palladium compounds of the types $PdX_2L_2$ and $PdL_4$, wherein X represents a halogen atom and L represents a ligand (for example triphenylphosphane, tri(o-tolyl)phosphane or tri(p-anisyl)phosphane), are preferred. The amount of palladium can be chosen such that 0.0001 to 1 mol % of palladium, based on the bromoaromatics employed, is present in the reaction mixture. This amount is preferably 0.001 to 0.1 mol %, particularly preferably 0.005 to 0.05 mol %.

Acrylic acid derivatives which can be employed are, for example, those of the formula (I)

(I)

in which
R represents CN or $COR^1$ wherein $R^1$ denotes OH, $O-C_6-C_{10}$-aryl, $O-C_1-C_{20}$-alkyl, $NH_2$, $NH-C_6-C_{10}$-aryl, $NH-C_1-C_{20}$-alkyl, $N-C_6-C_{10}$-aryl, $N-C_1-C_{20}$-alkyl-$C_6-C_{10}$-aryl or $N$-di-$C_1-C_{20}$-alkyl.

In formula (I) R preferably represents $COR^1$ where $R^1=O-C_1-C_{20}$-alkyl, particularly preferably $C_1-C_{10}$-alkyl.

Bromoaromtics which can be employed are, for example, bromobenzenes of the formula (II)

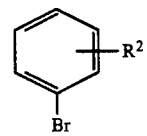
(II)

in which
$R^2$ represents hydrogen, $C_6-C_{10}$-aryl, $C_1-C_{20}$-alkyl, $OR^3$ or $NR^3_2$, where $R^3$ is hydrogen, $C_6-C_{10}$-aryl or $C_1-C_{20}$-alkyl.

In formula (II), $R^2$ preferably represents $OR^3$ or $NR^3_2$, where $R^3$=phenyl or $C_1-C_{10}$-alkyl, and $R^2$ particularly preferably represents methoxy.

Any desired molar ratio of bromoaromatic to acrylic acid derivative can be chosen. The reaction is preferably carried out at a molar ratio of bromoaromatic to acrylic acid derivative in the range from 1:0.7 to 1:3. This ratio is particularly preferably 1:0.8 to 1:1.2.

Possible inorganic bases for the process according to the invention are, for example, alkali metal and alkaline earth metal salts of weak acids, preferably alkali metal and alkaline earth metal bicarbonates and/or carbonates. Sodium carbonate is particularly preferably used. The ratio of bromoaromatic to base is preferably chosen such that 0.8 to 2, particularly preferably 0.9 to 1.3 equivalents of base are employed per mole of bromoaromatic.

If the process according to the invention is carried out in the presence of a phase transfer catalyst, phase transfer catalysts which are known per se are possible. In the context of the present invention, for example, crown ethers, ammonium salts or phosphonium salts, in each case substituted by organic radicals, and polyethylene glycols can be employed as phase transfer catalysts. Ammonium and phosphonium salts which contain as organic radicals $C_6-C_{10}$-aryl, $C_7-C_{12}$-aralkyl and/or $C_1$–$C_{20}$-alkyl radicals, and a halide ion, in particular chloride, as the anion, and polyethylene glycols having an average molecular weight of 200 to 1000 g/mol are preferred. Methyltrioctylammonium chloride and polyethylene glycol 400 are particularly preferably employed as the phase transfer catalyst. The amount of phase transfer catalyst can be, for example, 0.01 to 50 mol %, based on the bromoaromatics employed. This amount is preferably 0.1 to 15 mol %, particularly preferably 0.7 to 2 mol %.

If the process according to the invention is carried out in the presence of alcohols, $C_2$–$C_{24}$-alcohols, for example, can be employed for this. $C_4$–$C_{20}$-alcohols are preferred, and $C_5$–$C_{18}$-alcohols are especially preferred. The term "alcohols" is understood here as meaning mono- and polyols of the corresponding C number. Examples which may be mentioned are: 3-methyl-1-butanol, 2-ethyl-1-hexanol, 1-decanol, 1-dodecanol, 1-octadecanol, 1,12-octadecanediol, 2-ethyl-1,3-hexanediol, 1,2,3-propanetriol and 2,2-bis-(hydroxymethyl)-1,3-propanediol. Mixtures of such alcohols can of course also be used. The amount of alcohols can be varied within wide limits. It is preferably 0.1 to 2, particularly preferably 0.2 to 1 liter of alcohol per mole of bromoaromatic.

It is also possible to employ both, a phase transfer catalyst and alcohols, together. The amount of alcohol chosen can then be significantly smaller. In this case, it is in general sufficient to add 1 to 50 mol %, based on the bromoaromatics employed, preferably 3 to 30 mol % of alcohol.

The phosphane employed can be, for example, a phosphane of the formula (III)

(III)

in which
R$^4$, R$^5$ and R$^6$ independently of one another each represent $C_6$–$C_{10}$-aryl, $C_1$–$C_{20}$-alkyl, phosphino-$C_1$–$C_{20}$-alkyl or phosphino-$C_6$–$C_{10}$-aryl, each of which is optionally substituted by halogen, $C_1$–$C_{20}$-alkyl OR$^7$ or NR$^7_2$ (R$^7$=hydrogen or $C_1$–$C_{20}$-alkyl).

Preferably, in formula (III), R$^4$, R$^5$ and R$^6$ independently of one another represent $C_6$–$C_{10}$-aryl radicals which are substituted by $C_1$–$C_{20}$-alkyl and/or $C_1$–$C_{20}$-alkoxy and/or unsubstituted.

Particularly preferred phosphanes of the formula (III) are triphenylphosphane, tri-o-tolylphosphane, tri-p-anisylphosphane and bisdiphenylphosphinomethane.

Phosphanes can be employed in the process according to the invention, for example, in a molar ratio of palladium:phosphorus of 1:4 to 1:150. This ratio is preferably 1:10 to 1:100, particularly preferably 1:20 to 1:90.

The process according to the invention can be carried out, for example, at temperatures in the range from 100° to 300° C. Preferred temperatures are in the range from 120° to 250° C., and particularly preferred temperatures are in the range from 140° to 190° C. The process according to the invention is usually carried out under normal pressure. However, it can also be carried out under reduced or increased pressure. The use of increased pressure is particularly indicated if it is intended to carry out the reaction at a temperature at which the individual constituents of the reaction mixture boil under normal pressure.

If higher alcohols which are not of unlimited miscibility with water are employed in the process according to the invention, it is in general advantageous to carry out the reaction at the reflux temperature of the reaction mixture and for the water of reaction which forms to be separated off continuously, for example with the aid of a water separator.

The process according to the invention is in general carried out under a protective gas, for example nitrogen, and while stirring.

Using the process according to the invention, for example, cinnamic acid derivatives of the formula (IV)

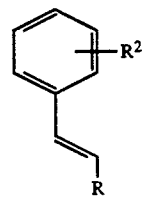

in which the symbols used have the meaning given in the case of formula (I) and (II), can be prepared.

After the process according to the invention has been carried out, the inorganic salts formed can be separated off, for example, by simple filtration or filtration with suction. It is also possible to allow the salts to settle and to decant off the remaining reaction mixture.

One possible embodiment of the process according to the invention is explained below using the reaction of 4bromoanisole with 2-ethylhexyl acrylate by way of example:

4-Bromoanisole, 2-ethylhexyl acrylate, sodium carbonate and methyl-tri-n-octylammonium chloride are initially introduced into the reaction vessel. Triphenylphosphane and palladium(II) chloride are added in a molar ratio of palladium:phosphorus of 1:40. The sequence of addition of these components can be changed as desired. The mixture is then heated to 150° to 160° C., under nitrogen and while stirring vigorously. When it has been established that no further 4-bromoanisole reacts, the reaction is terminated, that is to say the mixture is cooled to room temperature. The sodium bromide which has precipitated is then filtered off with suction, and the filter cake is washed with an organic solvent (for example petroleum ether) in order to remove adhering product. The resulting filtrate can be freed from the solvent and distilled in vacuo.

It is surprising that the palladium-catalysed reaction according to the invention of less reactive bromoaromatics with acrylic acid derivatives in the presence of inorganic bases present in undissolved form and with the addition of a phase transfer catalyst and/or alcohols produces high space/tithe yields, even when only very small amounts of palladium catalyst are employed.

It is likewise surprising that the addition of phosphane in a large excess significantly increases the rate of reaction. It is known that palladium complexes which catalyse the arylation of olefins are surrounded by not more than 4 phosphane ligands, so that an optimum ratio of palladium:phosphorus of 1:4 was to be expected. Since at low concentrations of palladium a small excess of phosphane is usually used, so that the formation of the 1:4 complexes is ensured in every case, it would not have been surprising to obtain advantages by increasing the ratio of palladium:phosphorus to, for example, 1:8. However, further increase of the excess of phosphanes to molar ratios of palladium:phosphane of more than 1:10 and the associated increase in the rate of reaction was not to be foreseen, especially since, under other reaction conditions, a molar ratio of palladium:phosphane of 1:2 is described as the optimum (J. Am. Chem. Soc. 96., 1133–1136 (1974)), and when palladium:phosphane are employed in a molar ratio of 1:8, no noticeable changes compared with the procedure at a molar ratio of 1:2 have been found (J. Organomet. Chem. 258, 101–108 (1983)).

The process according to the invention renders possible the preparation of cinnamic acid derivatives, in particular the preparation of 2-ethylhexyl p-methoxycinnamate and isoamyl 4-methoxycinnamate, under advantageous reaction conditions, no particular effort being necessary for handling auxiliaries (bases and solvents). The bases, phase transfer catalysts and alcohols required are readily accessible and inexpensive.

The process according to the invention is considerably more economical and achieves a higher space/time yield, compared with the processes of the prior art.

Cinnamic acid derivatives, in particular 2-ethylhexyl and isoamyl p-methoxycinnamate, can be employed, for example, as UV absorbers in cosmetics (see U.S. Pat. No. 5,008,100 and U.S. Pat. No. 4,810,490).

EXAMPLE 1

187.04 g of 4-bromoanisole, 202.7 g of 2-ethylhexyl acrylate, 53 g of sodium carbonate and 4.42 g of methyl-tri-n-octylammonium chloride were initially introduced into a four-necked round-bottomed flask, and 2.63 g of triphenylphosphane and 56 mg of palladium acetate (0.025 mol %, based on the 4-bromoanisole) were added. The mixture was heated to 150° to 160° C., under nitrogen and whilst stirring vigorously. After 20 hours the conversion according to gas chromatography was 98%, based on the 4-bromoanisole employed.

The sodium bromide which had precipitated (93.5 g =91% of theory) was filtered off with suction and washed with a little hexane. The filtrate was freed from the hexane and distilled in vacuo. A yield of isolated 2-ethylhexyl p-methoxycinnamate of 187.1 g resulted.

EXAMPLE 2

COMPARISON EXAMPLE

The procedure was as in Example 1, but only 263 mg of triphenylphosphane were added, so that a molar ratio of palladium:phosphorus of 1:4 resulted. After 20 hours the conversion according to gas chromatography was 30%, based on the 4-bromoanisole employed.

EXAMPLE 3

The procedure was as in Example 1 but, instead of palladium acetate, 44 mg of palladium chloride were added. After 20 hours the conversion according to gas chromatography was 95%, based on the 4-bromoanisole employed.

EXAMPLE 4

The procedure was as in Example 1 but, instead of methyl-tri-n-octylammonium chloride, 4 g of polyethylene glycol 400 were added. After 4 hours the conversion according to gas chromatography was 89%, based on the 4-bromoanisole employed.

EXAMPLE 5

A reaction mixture of 18.7 g of 4-bromoanisole, 20.3 g of 2-ethylhexyl acrylate, 6.36 g of sodium carbonate, 0.0025 g [=0.01 mol %]of palladium(II) acetate and 0.026 g of triphenylphosphane (molar ratio of Pd:phosphorus=1:10) in 80 ml of 2-ethyl-1-hexanol was heated to 150° C. under nitrogen. The conversion of bromoanisole, determined by gas chromatography, was 51% after 4 hours.

EXAMPLE 6

The procedure was as in Example 5, but 0.105 g of triphenylphosphane was employed (=molar ratio of Pd:phosphorus of 1:40). The conversion was 98% after 4 hours.

EXAMPLE 7

The procedure was as in Example 6, but the reaction was carried out at the reflux temperature of the reaction mixture. The conversion was 100% after 2 hours.

EXAMPLE 8

A reaction mixture of 18.7 g of 4-bromoanisole, 20.3 g of 2-ethylhexyl acrylate, 6.36 g of sodium carbonate, 0,056 g (0,025 mol %) of palladium(II) acetate and 0,088 g of tri(p-anisyl)phosphane in 80 ml of 2-ethyl-1-hexanol was heated to 180° C. under nitrogen. The conversion of bromoanisole, determined by gas chromatography, was 99% after 2 hours.

EXAMPLE 9

A reaction mixture of 18.7 g of 4-bromoanisole, 20.3 g of 2-ethylhexyl acrylate, 6.36 g of sodium carbonate, 0.0175 g (0.025 mol %) of bis(triphenylphosphane)-palladium(II) chloride and 0.0525 g of triphenylphosphane (molar ratio of Pd:phosphorus of 1:10 in total) in 80 ml of 2-ethyl-1-hexanol was heated to 150° C. under nitrogen. The conversion of bromoanisole, determined by gas chromatography, was 99% after 4 hours.

EXAMPLE 10

A reaction mixture of 18.7 g of 4-bromoanisole, 20.3 g of 2-ethylhexyl acrylate, 6.36 g of sodium carbonate, 0.0056 g of palladium(II) acetate and 0.262 g of triphenylphosphane (molar ratio of Pd:phosphorus of 1:40) in 10 ml of 2-ethyl-1-hexanol was heated to 150° C. under nitrogen. The conversion of bromoanisole, determined by gas chromatography, was 53% after 3 hours.

EXAMPLE 11

The procedure was as in Example 10, but 20 ml of 2-ethyl-1-hexanol were employed. The conversion was 91% after 3 hours.

EXAMPLE 12

The procedure was as in Example 10, but 40 ml of 2-ethyl-1-hexanol were employed. The conversion was 86% after 2 hours and 100% after 3 hours.

EXAMPLE 13

The procedure was as in Example 10, but 80 ml of 2-ethyl-1-hexanol were employed. The conversion after 2 hours was 97%.

EXAMPLE 14

A reaction mixture of 18.7 g of 4-bromoanisole, 15.6 g of amyl acrylate, 6.36 g of sodium carbonate, 0.0056 g (0.025 mol %) of palladium(II) acetate, 0.262 g of triphenylphosphane (molar ratio of Pd:phosphorus of 1:40) and 80 ml of isoamyl alcohol was heated to the reflux temperature under nitrogen. The conversion of 4-bromoanisole was 94% after 6 hours.

EXAMPLE 15

167 g of 4-bromoanisole, 184.3 g of 2-ethylhexyl acrylate, 664 g of 2-ethyl-1-hexanol, 55.7 g of sodium carbonate and 0.66 g of triphenylphosphane were initially introduced into a 4 l flask. After the mixture had been stirred at room temperature for a few minutes a solution of 0,056 g of palladium(II) acetate in 20 g of 4-bromoanisole was added. The reaction mixture was then stirred thoroughly at the reflux temperature under a nitrogen atmosphere for 7 hours. After cooling to room temperature, the reaction mixture was filtered and the filter residue was washed with 150 g of 2-ethyl-1-hexanol. The resulting residue on the filter was dried in vacuo. 101.7 g of solid (mainly sodium bromide and sodium carbonate) were thus obtained.

Fractional distillation of the filtrate gave 775.7 g of 2-ethyl-1-hexanol and 237 g of 2-ethylhexyl 4-methoxycinnamate, corresponding to 81.6% of theory.

EXAMPLE 16

171.7 g of 4-bromoanisole, 332 g of 2-ethyl-1-hexanol, 63.6 g of sodium carbonate and 2.1 g of triphenylphosphane (molar ratio of Pd:phosphorus of 1:80) were initially introduced into a 2 l flask, and the mixture was heated at reflux for 15 minutes, while passing in nitrogen. A solution of 0.022 g of palladium(II) acetate in 15.3 g of 4-bromoanisole and 203 g of 2-ethylhexyl acrylate were then added. After refluxing for 3 hours using a water separator (to remove the water formed during the reaction), the conversion of 4-bromoanisole was 90%.

Filtration of the reaction mixture and distillation of the filtrate gave a yield of 2-ethylhexyl 4-methoxycinnamate of 77% of theory, based on the 4-bromoanisole employed.

EXAMPLE 17

A reaction mixture of 18.7 g of 4-bromoanisole, 20.3 g of 2-ethylhexyl acrylate, 6.36 g of sodium carbonate, 0.0025 g of palladium(II) acetate, 0.21 g of triphenylphosphane and 2.0 g of polyethylene glycol 400 was heated to 170° C. under nitrogen. The conversion of bromoanisole, determined by gas chromatography, was 97% after 3 hours.

EXAMPLE 18

The procedure was as in Example 17, but 1.95 g of 2-ethyl-1-hexanol were added. The conversion after 2 hours was 96%.

EXAMPLE 19

The procedure was as in Example 17, but 6.5 g of 2-ethyl-1-hexanol were added. The conversion after 3 hours was 97%.

EXAMPLE 20

A reaction mixture of 18.7 g of 4-bromoanisole, 20.3 g of 2-ethylhexyl acrylate, 6.36 g of sodium carbonate, 0.0025 g of palladium(II) acetate, 0.21 g of triphenylphosphane and 1.43 g of 1,12-octadecanediol was heated to 170° C. under nitrogen. The conversion of bromoanisole, determined by gas chromatography, was 72% after 3 hours.

EXAMPLE 21

A reaction mixture of 18.7 g of 4-bromoanisole, 20.3 g of 2-ethylhexyl acrylate, 6.36 g of sodium carbonate, 0.0025 g of palladium(II) acetate, 0.21 g of triphenylphosphane and 5.0 g of polyethylene glycol 1000 was heated to 170° C. under nitrogen. The conversion of bromoanisole, determined by gas chromatography, was 100% after 2 hours. After vacuum distillation, an 82% yield of 2-ethylhexyl 4-methoxycinnamate, based on the 4-bromoanisole reacted, was obtained.

EXAMPLE 22

187.0 g of 4-bromoanisole, 202.7 g of 2-ethylhexyl acrylate, 63.8 g of sodium carbonate, 7.3 g of 2-ethylhexane-1,3-diol and 20 g of polyethylene glycol 400 were initially introduced into a four-necked round-bottomed flask, and 2.1 g of triphenylphosphane and 0.023 g of palladium(II) acetate (molar ratio of Pd:phosphorus of 1:80) were added.

The mixture was heated to 160°–170° C. for 3.5 hours, under nitrogen and while stirring vigorously. After this time the conversion was 95%, based on the 4-bromoanisole employed.

After filtration with suction and distillation in vacuo (0.1 mbar), a yield of 88% of theory in total (based on the 4-bromoanisole reacted) of 2-ethylhexyl 4-methoxycinnamate was isolated.

We claim:

1. Process for the preparation of cinnamic acid derivatives from bromoaromatics and acrylic acid derivatives in the presence of palladium catalysts and a phosphane, characterised in that it is carried out in the presence of an inorganic base, a large excess (based on the palladium) of phosphane, and alcohols and/or a phase transfer catalyst.

2. Process according to claim 1, characterised in that palladium compounds of oxidation level 0 and/or +2 are employed as palladium catalysts in amounts of 0.0001 to 1 mol % of palladium (based on the bromoaromatics employed).

3. Process according to claims 1, characterised in that an acrylic acid derivative of the formula

 (I)

in which
R represents CN or $COR^1$, wherein $R^1$ denotes OH, O-$C_6$-$C_{10}$-aryl, O-$C_1$-$C_{20}$-alkyl, $NH_2$, NH-$C_6$-$C_{10}$-aryl, NH-$C_1$-$C_{20}$-alkyl, N-$C_6$-$C_{10}$-aryl, N-$C_1$-$C_{20}$-alkyl-$C_6$-$C_{10}$aryl or N-di-$C_1$-$C_{20}$-alkyl,
is employed.

4. Process according to claim 1, characterised in that a bromobenzene of the formula (II)

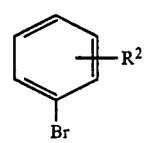 (II)

in which
R² represents hydrogen, $C_6$–$C_{10}$-aryl, $C_1$–$C_{20}$-alkyl, $OR^3$ or $NR^3{}_2$, where $R^3$ is hydrogen, $C_6$–$C_{10}$-aryl or $C_1$–$C_{20}$-alkyl,
is employed as the bromoaromatic, and a molar ratio of bromoaromatic to acrylic acid derivative in the range from 1:0.7 to 1:3 is maintained.

5. Process according to claim 1, characterised in that alkali metal and/or alkaline earth metal salts of weak acids are employed as the inorganic base in amounts of 0.8 to 2 mol (per mole of bromoaromatic).

6. Process according to claim 1, characterised in that crown ethers, ammonium or phosphonium salts, in each case substituted by organic radicals, or polyethylene glycols are employed as phase transfer catalysts in an amount of 0.01 to 50 mol % (based on the bromoaromatic employed).

7. Process according to claim 1, characterised in that it is carried out in the presence of one or more $C_2$–$C_{24}$-alcohols, 3 to 30 mol % of these alcohols (based on the bromoaromatic employed) being employed in the presence of phase transfer catalysts and 0.1 to 2 of these alcohols per mole of bromoaromatic being employed in the absence of phase transfer catalysts.

8. Process according to claim 1, characterised in that a phosphane of the formula (III)

in which
R⁴, R⁵ and R⁶ independently of one another each represent $C_6$–$C_{10}$-aryl, $C_1$–$C_{20}$-alkyl, phosphino-$C_1$–$C_{20}$-alkyl or phosphino-$C_6$–$C_{10}$-aryl, each of which is optionally substituted by halogen, $C_1$–$C_{20}$-alkyl $OR^7$ or $NR^7{}_2$ ($R^7$=hydrogen or $C_1$–$C_{20}$-alkyl),
is employed, and a molar ratio of palladium:phosphorus of 1:4 to 1:150 is maintained.

9. Process according to claim 1, characterised in that it is carried out at temperatures in the range from 100° to 300° C.

10. Process according to claim 1, characterised in that it is carried out under a protective gas and while stirring.

* * * * *